(12) United States Patent
Seok et al.

(10) Patent No.: US 8,375,774 B2
(45) Date of Patent: Feb. 19, 2013

(54) SCRATCH TESTING APPARATUS FOR PERFORMING SCRATCHING TEST WHILE GRADUALLY INCREASING OR DECREASING LOAD

(75) Inventors: Changsung Seok, Gwacheon-si (KR); Hongsun Park, Pohang-si (KR); Jongil Weon, Seoul (KR)

(73) Assignee: Sungkyunkwan University Foundation for Corporate Collaboration (KR)

( * ) Notice: Subject to any disclaimer, the term of this patent is extended or adjusted under 35 U.S.C. 154(b) by 561 days.

(21) Appl. No.: 12/708,229

(22) Filed: Feb. 18, 2010

(65) Prior Publication Data

US 2010/0206041 A1    Aug. 19, 2010

(51) Int. Cl.
*G01N 3/46* (2006.01)
*G01N 3/56* (2006.01)

(52) U.S. Cl. .................................. 73/81; 73/7
(58) Field of Classification Search ............ 73/7, 78, 73/81, 150 R
See application file for complete search history.

(56) References Cited

U.S. PATENT DOCUMENTS

| | | | | |
|---|---|---|---|---|
| 2,279,264 A | * | 4/1942 | Hoffman | 73/78 |
| 7,302,831 B2 | * | 12/2007 | Moyse et al. | 73/81 |
| 7,316,155 B2 | * | 1/2008 | Chudoba et al. | 73/81 |
| 8,215,163 B2 | * | 7/2012 | Zhang | 73/7 X |
| 8,266,944 B2 | * | 9/2012 | Kwon et al. | 73/7 |
| 2009/0293585 A1 | * | 12/2009 | Kwon et al. | 73/7 |
| 2010/0152361 A1 | * | 6/2010 | Weaver et al. | 524/528 |

FOREIGN PATENT DOCUMENTS

| | | | | |
|---|---|---|---|---|
| DE | 1548305 B | * | 5/1974 | |
| DE | 19618000 C1 | * | 8/1997 | |
| DE | 19925310 A1 | * | 12/2000 | |
| JP | 2007083270 A | * | 4/2007 | |
| KR | 2006023214 A | * | 3/2006 | |
| KR | 2010094770 A | * | 8/2010 | |
| WO | WO 0216907 A1 | * | 2/2002 | |

* cited by examiner

*Primary Examiner* — Thomas P Noland
(74) *Attorney, Agent, or Firm* — Cantor Colburn LLP

(57) ABSTRACT

A scratch testing apparatus for performing a scratching test while gradually increasing or decreasing a load, in which a pressure applied to the surface of a test specimen gradually increases or decreases as a head unit, to which a tip is attached, moves horizontally. The scratching testing apparatus includes a head unit having a bottom to which a tip attached; a guiding unit for guiding the head unit to move horizontally; and a pressure changing unit for changing pressure applied to the tip while the head unit is moving along the guiding unit. Therefore, the scratch testing apparatus may perform a scratching test as gradually increasing or gradually decreasing a load applied to the test specimen by the tip by moving the head unit, to which the tip is attached, horizontally.

5 Claims, 3 Drawing Sheets

SCRATCH TESTING APPARATUS FOR PERFORMING SCRATCHING TEST WHILE GRADUALLY INCREASING OR DECREASING LOAD

CROSS-REFERENCE TO RELATED PATENT APPLICATIONS

This application claims the benefit of Korean Patent Application No. 2009-0013911, filed on Feb. 19, 2009, in the Korean Intellectual Property Office, the disclosure of which is incorporated herein in its entirety by reference.

BACKGROUND OF THE INVENTION

1. Field of the Invention

The present invention relates to a scratch testing apparatus for performing a scratching test while gradually increasing or decreasing a load. and more particularly, to a scratch testing apparatus, in which load applied using a tip gradually increases or decreases as a tester head, to which the tip is attached, moves horizontally, so that scratching operation may be performed as changing a load applied to a test specimen.

2. Description of the Related Art

A tape testing method, a bending test, a press-fitting testing method and a scratching testing method are included as examples of testing methods generally used for testing adhesiveness between an object material and a thin film of coating or paint performed to maintain and reinforce characteristics of the object material. A tape testing method is to determine whether coating or paint comes off or not when a tape (an adhesive tape) is attached on and then detached from a surface of an object material. The bending test is the method of measuring a bending load at which a coating or paint comes off. A press-fitting testing method is to determine adhesiveness of a coating or paint through inspecting a crack and an indentation existed on a coated or painted surface after an object material is press-fitted. Finally, a scratching testing is a method of determining the critical load based on scratches formed by scratching a coated or painted surface.

Here, the scratching testing method is convenient and provides quantized measurement. Therefore, the scratching testing method is the most widely used in industries.

During a scratching test, adhesiveness between materials is determined based on color shifting of a coating, paint, or a thin film or a change of plasticity which appears on the surfaces of the materials.

A method of applying a predetermined load on a surface and scratching the surface is used to determine the adhesiveness. However, a number of tests should be performed and a lot of test specimens are needed in order to determine a critical load.

Therefore, scratching testing method, in which a load applied to a test specimen changes as a tip moves from a beginning point to a ending point of the scratching, is standardized and disclosed in ASTM D7027, ISO 1518, and ISO 12137-2.

According to the method above, a load at the time of generating a deformation by a scratch on a surface is detected, and thus adhesiveness between the surface and the material and a property of the material are determined by measuring the load.

According to the ASTM D7027 standards, the critical load shall be determined by gradually increasing a load from 2N to 50N with respect to a displacement of 100 mm at a rate of 100 mm/s and observing whitening phenomenon of the material.

Furthermore, according to ISO 1518 and ISO 12137-2 standards, a scratching test shall be performed by forming a scratch at a rate of 200 mm/s to determine the critical load of scratching paint or a coated plastic.

However, since the scratching method shall be performed at a relatively fast rate, it is difficult to control the load and displacement of a testing apparatus, and it is difficult to synchronize the beginning of movements, transportations, and the stopping of movements along the vertical axis and the horizontal axis.

SUMMARY OF THE INVENTION

To solve the above and/or other problems, the present invention provides a scratch testing apparatus for performing a scratching test while gradually increasing or decreasing a load.

According to an aspect of the present invention, there is provided scratching testing apparatus including a head unit, wherein a tip is attached to the bottom of the head unit; a guiding means 22 for guiding the head unit 10 to move horizontally; and a pressure changing means for changing pressure applied to the tip while the head unit moves along a guiding means, and the pressure changing means including an inclined rail slantingly installed above the head unit and a spring unit installed in the head unit.

Furthermore, a unit to be pushed is installed below the inclined rail, and a vertical position adjusting unit is formed on the bottom of the unit to be pushed.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
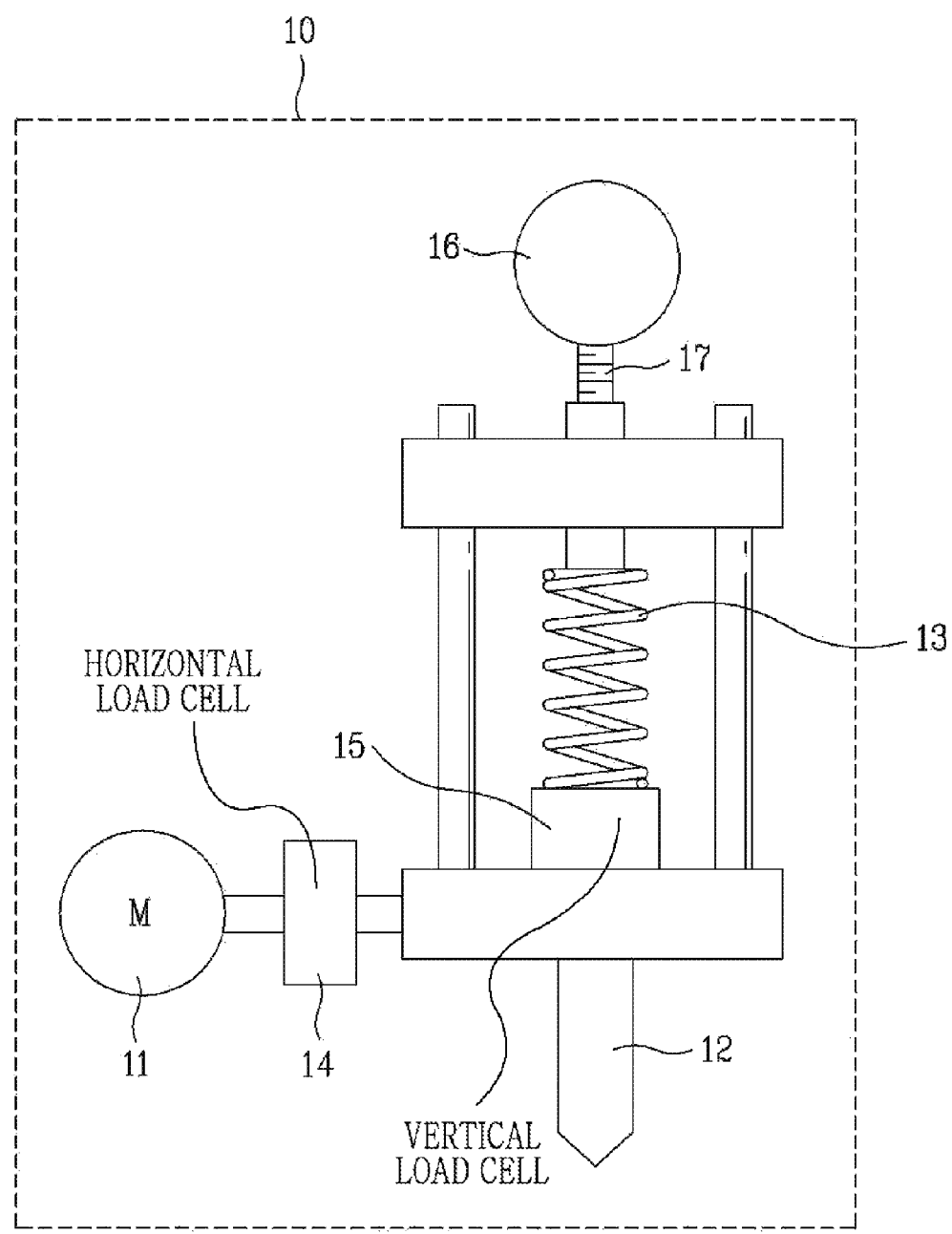
FIG. 1 is a view of a head unit of the scratching testing apparatus according to the present invention.

Hereinafter, the scratch testing apparatus according to the present invention will be described in detail by explaining exemplary embodiments of the invention with reference to the attached drawings. The same reference numerals in the drawings denote the same or similar elements.

Figure 2:
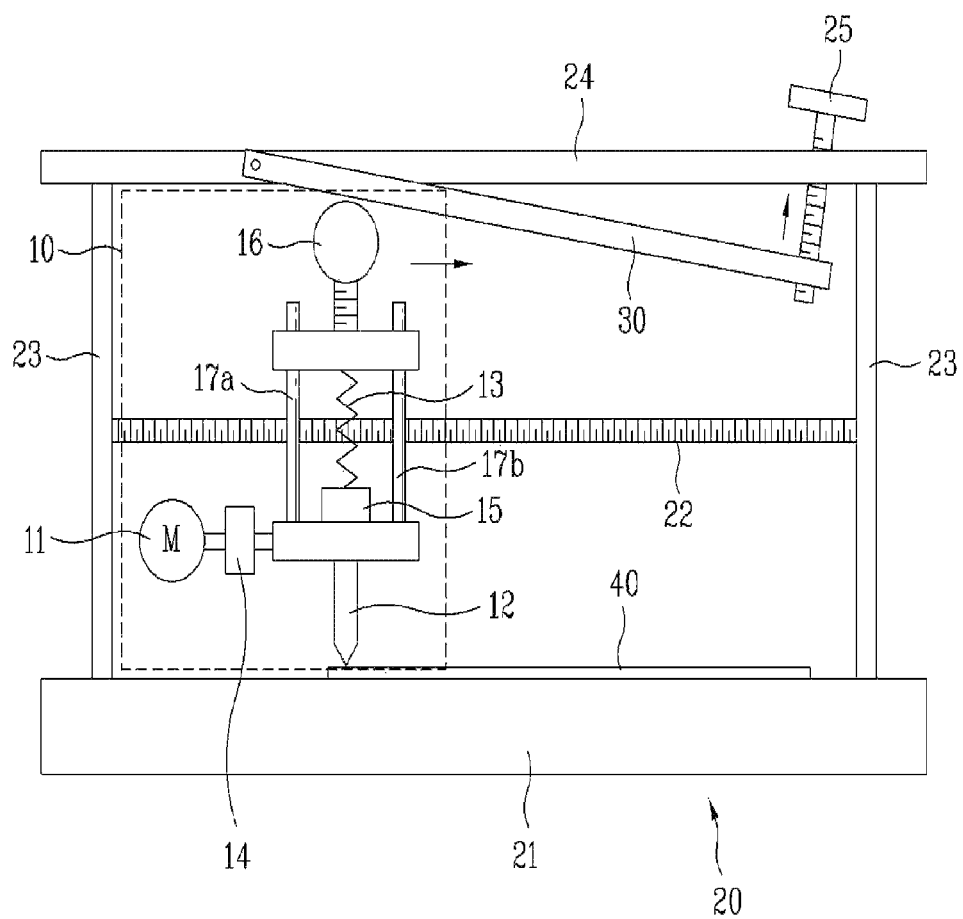
FIG. 2 is a view of the scratching testing apparatus according to the present invention.
Figure 3:
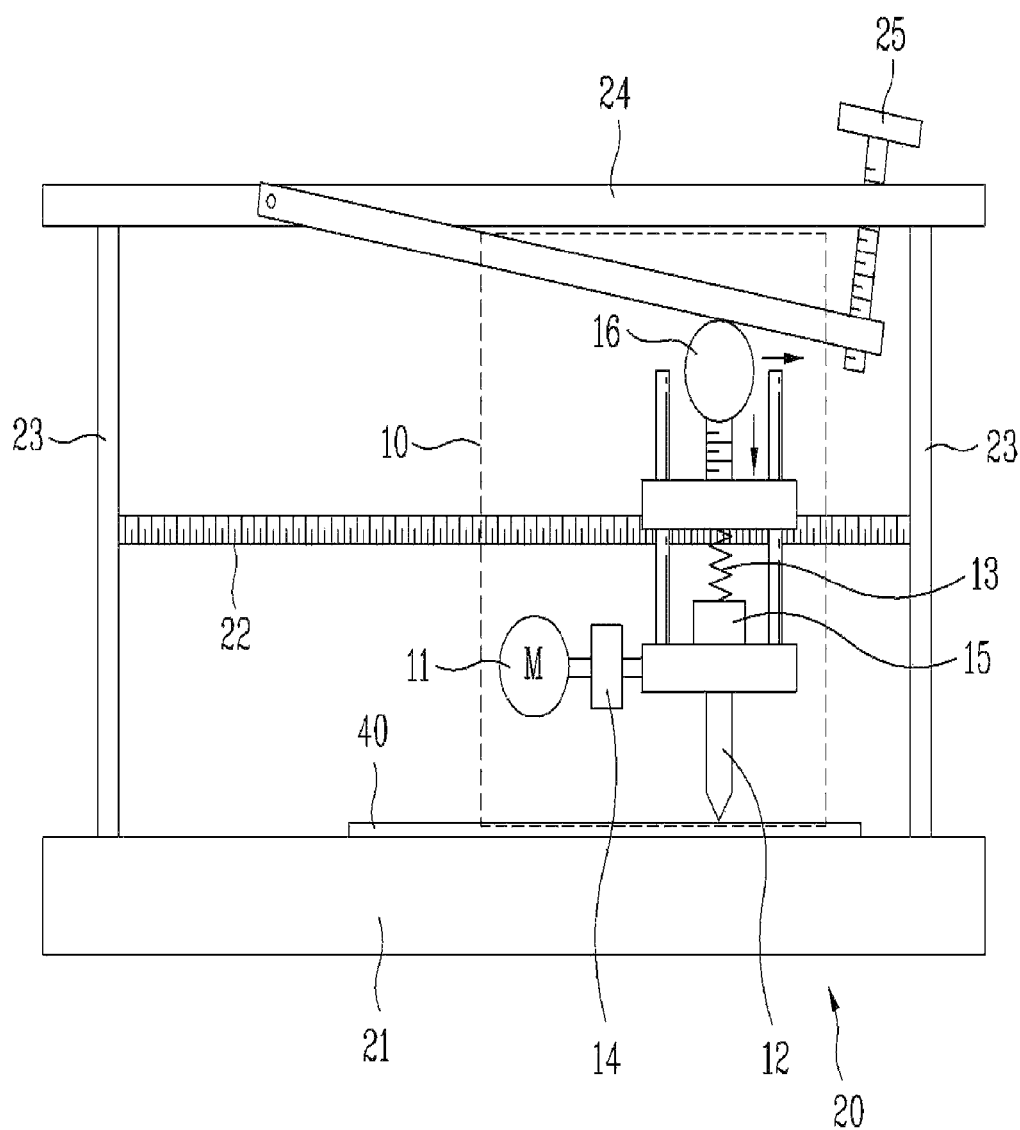
FIG. 3 is a view of operations of the scratch testing apparatus according to the present invention.

FIG. 1 is a diagram showing a head unit 10 of the scratch testing apparatus according to the present invention. FIG. 2 is a diagram showing the scratch testing apparatus according to the present invention. FIG. 3 is a diagram showing operations of the scratch testing apparatus according to the present invention.

In the scratch testing apparatus to the present invention, a unit to be pushed, which is vertically pushed and is moved downward when its top is depressed, is formed in the head unit 10, which moves horizontally, as shown in FIG. 1.

The unit to be pushed is a bearing unit 16, which has a shape for minimizing friction while being moved, and thus friction between the bearing unit 16 and a surface may be minimized.

Although the bearing unit 16 is introduced as an example of the unit to be pushed, the present invention is not limited thereto, and the unit to be pushed may be formed of a sliding member or a vertical rod. In other words, as long as friction may be minimized by the unit to be pushed at surfaces contacting each other, any of various members may be used as the unit to be pushed.

A spring unit 13, which works in linkage with the bearing unit 16, is formed below the unit to be pushed, that is, the bearing unit 16.

The bearing unit 16, which is above the spring unit 13, presses the spring unit 13 downward by a height in which the bearing unit 16 is pushed.

At this time, the spring unit 13 vertically pressed by the bearing unit 16 is formed to press a tip unit 12, which is connected to the spring unit 13 to work in linkage with the spring unit 13, vertically downward.

A damper is attached on top of the spring unit 13 to prevent vibration or the like when the spring unit 13 is displaced in horizontal direction while being vertically pressed by the bearing unit 16.

As the bearing unit 16 of the head unit 10 is pressed and presses the spring unit 13 downward, elastic reaction force generated by the spring unit 13 is applied to the tip unit 12, and thus the tip unit 12 applies a vertical load to a test specimen 40, which is disposed on a test bed 21 formed below a body 20.

Although not shown, the spring unit 13, which applies elastic load to press the tip unit 12 of the head unit 10 downward, may be easily replaced with various types of springs having different spring coefficients, and thus a starting load and an ending load may be changed as desired.

The tip unit 12 of the head unit 10, which works as described above, is installed such that the tip unit 12 is moved horizontally by a motor 11 simultaneously as the tip unit 12 is vertically pressed.

Furthermore, a vertical load cell 15 for detecting amount of pressure applied by the spring unit 13 is installed on the spring unit 13, which is attached to the head unit 10.

Therefore, a vertical load applied to the tip unit 12 may be detected by using the vertical load cell 15.

Furthermore, a horizontal load cell 14 is attached to the motor 11, and thus, when the tip unit 12 moves on the surface of the test specimen 40, which is disposed and fixed on the test bed 21, as scratching the surface of the test specimen 40, a horizontal load applied in the direction in which the tip unit 12 moves may be detected.

As shown in FIG. 2, the head unit 10 including the tip unit 12, which works as described above, is installed to move along a ball screw 22, which is formed between vertical frames 23 on the test bed 21 of the body 20.

When the head unit 10 is attached to the ball screw 22 of the body 20, the head unit 10 is horizontally moved along the ball screw 22 by the motor 11.

When the head unit 10 is smoothly slid without vibration by the motor 11 and is moved horizontally along the ball screw 22, the bearing unit 16 of the head unit 10 is horizontally slid and moved along an inclined rail 30 formed on an upper frame 24 of the body 20, where the bearing unit 16 continues to contact the bottom surface of the inclined rail 30.

In other words, the bearing unit 16 is vertically pressed while being horizontally moved along the inclined rail 30 at a tilt corresponding to the angle of inclination of the inclined rail 30.

Accordingly, the bearing unit 16, which is moved by the motor 11, moves along the bottom surface of the inclined rail 30, which is inclined by a predetermined angle with respect to the horizontal direction.

The spring unit 13 formed below the bearing unit 16 is gradually pressed in a vertical direction as the bearing unit 16 is moved along the inclined rail 30.

As shown in FIG. 3, due to elastic reaction force of the spring unit 13, pressure is applied to the tip unit 12 formed below the spring unit 13.

When a pressure is applied to the tip unit 12, load applied to the surface of the test specimen 40 disposed on the test bed 21 increases, and thus the surface of the test specimen 40 is scratched.

Therefore, pressure applied by the tip unit 12 of the head unit 10 gradually increases (as the bearing unit 16 moves from an end of the inclined rail 30 to the opposite end of the inclined rail 30), and thus the surface of the test specimen 40 is scratched. In other words, the scratching testing method according to the present invention begins when the inclined rail 30 is installed on the upper frame 24 such as to be inclined downward as going toward the right side of FIGS. 2 and 3 as shown in FIGS. 2 and 3. Therefore, as the head unit 10 moves horizontally, the vertical position of the head unit 10 is lowered, and thus the spring unit 13 is further compressed.

Pressure applied to the tip unit 12 as the inclined rail 30 is slantingly installed as described above is transmitted to the tip unit 12 as elastic reaction force of the spring unit 13, and thus the head unit 10 moves horizontally while press-fitting the test specimen 40. Therefore, the surface of the test specimen 40 is scratched, and also a vertical load applied to the test specimen 40 increases.

According to the present invention, the position and the angle of inclination of the inclined rail 30 may be changed, and thus a scratching test may be performed with a desired load applied when the scratching test begins or ends.

Furthermore, a screw-like vertical position adjusting unit 17 is formed on the bottom of the bearing unit 16. Therefore, when the vertical position adjusting unit 17 is rotated in a first direction, for example, the bearing unit 16 may rise, and thus the spring unit 13, which is formed below the bearing unit 16 to work in linkage with the bearing unit 16, and the tip unit 12, which is formed below the spring unit 12, may also rise.

Furthermore, when the vertical position adjusting unit 17, which is attached to the bottom of the bearing unit 16 so as to be integrally formed with the bearing unit 16, is rotated in a second direction, which is opposite to the first direction, the tip unit 12 may be lowered.

Therefore, since the vertical location of the tip unit 12 may be easily adjusted by using the vertical position adjusting unit 17 as described above, the scratch testing apparatus of the present invention can be properly applied even if the thickness of the test specimen 40 on the test bed 21 is changed.

While this invention has been particularly shown and described with reference to exemplary embodiments thereof, it will be understood by those skilled in the art that various changes in form and details may be made therein without departing from the spirit and scope of the invention as defined by the appended claims.

For example, although a case in which a vertical load applied to the test specimen 40 by the tip unit 12 increases as the head unit 10 moves horizontally is described in the above embodiment, a case where a load applied by the tip unit 12 gradually decreases as the inclined rail 30 is inclined oppositely as compared to the case shown in FIGS. 2 and 3, that is, the incline rail 30 is inclined upward as going toward the right side of FIGS. 2 and 3 may be considered.

What is claimed is:

1. A scratch testing apparatus for performing a scratching test while gradually increasing or decreasing a load comprising:

a head unit comprising a bottom to which a tip attached;

a guiding unit for guiding the head unit to move horizontally; and a pressure changing unit for changing pressure applied to the tip while the head unit is moving along the guiding unit, wherein the pressure changing unit comprises:

an inclined rail slantingly installed above the head unit; and a spring unit installed in the head unit.

2. The scratching testing apparatus of claim 1, further comprising a unit to be pushed, which contacts a bottom surface of the inclined rail.

3. The scratching testing apparatus of claim 2, wherein a vertical position adjusting unit is formed on a bottom of the unit to be pushed.

4. The scratching testing apparatus of claim 1, wherein the spring unit is replaceable with a spring having a different spring coefficient.

5. The scratching testing apparatus of claim 1, wherein a desired load to be applied when the scratching test begins or ends is changed by adjusting the angle of inclination of the inclined rail to perform the scratching test with gradually increasing or gradually decreasing load.

* * * * *